United States Patent
Couvillon, Jr. et al.

(10) Patent No.: US 8,888,684 B2
(45) Date of Patent: Nov. 18, 2014

(54) MEDICAL DEVICES WITH LOCAL DRUG DELIVERY CAPABILITIES

(75) Inventors: Lucien A. Couvillon, Jr., Concord, MA (US); Michael S. Banik, Bolton, MA (US); Samuel Sheng-Ping Zhong, Shrewsbury, MA (US)

(73) Assignee: Boston Scientific Scimed, Inc., Maple Grove, CA (US)

(*) Notice: Subject to any disclaimer, the term of this patent is extended or adjusted under 35 U.S.C. 154(b) by 2075 days.

(21) Appl. No.: 11/390,401

(22) Filed: Mar. 27, 2006

(65) Prior Publication Data
US 2007/0225564 A1 Sep. 27, 2007

(51) Int. Cl.
*A61B 1/04* (2006.01)
*A61M 31/00* (2006.01)
(Continued)

(52) U.S. Cl.
CPC .............. *A61B 1/012* (2013.01); *A61N 1/306* (2013.01); *A61B 1/2736* (2013.01); *A61B 1/31* (2013.01); *A61B 5/4839* (2013.01); *A61M 2025/0057* (2013.01)
USPC ............. 600/114; 604/500; 604/501; 607/40; 607/46; 607/116; 607/133; 623/1.42; 623/1.44; 623/1.45; 623/1.46

(58) Field of Classification Search
CPC ...... A61B 1/00082; A61B 1/01; A61B 1/273; A61B 1/2733; A61B 1/2736; A61B 1/0058; A61B 1/0053; A61N 1/0412; A61N 1/0416; A61N 1/042; A61N 1/0424; A61N 1/0428; A61N 1/0432; A61N 1/0436; A61N 1/044; A61N 1/0444; A61N 1/0448; A61N 1/0452; A61N 1/0456; A61N 1/046; A61N 1/0464; A61N 1/0468
USPC ................. 600/104, 121, 128, 114–116, 118, 600/139–140; 604/20, 890.1, 21; 623/1.42–1.47; 607/39–41, 46, 50, 607/115, 116, 133, 138
See application file for complete search history.

(56) References Cited

U.S. PATENT DOCUMENTS 3,266,059 A 8/1966 Stelle
3,470,876 A 10/1969 Barchilon
(Continued)

FOREIGN PATENT DOCUMENTS

EP 0 689 851 A1 1/1996
EP 1 300 883 A2 4/2003
(Continued)

OTHER PUBLICATIONS

Brannon-Peppas, L., "Polymers in Controlled Drug Delivery," *Medical Plastics and Biomaterials Magazine*, Nov. 1997, <http://www.devicelink.com/grabber.php3?URL=http://www.devicelink.com/mpb/archive/97/11/003.html>[retrieved Jul. 17, 2006].
(Continued)

*Primary Examiner* — Ryan Henderson
(74) *Attorney, Agent, or Firm* — Kacvinsky Daisak Bluni PLLC

(57) ABSTRACT

A medical device, for example, an endoscope or catheter, includes local drug delivery capabilities for selectively delivering at least one drug in vivo. The local drug delivery may occur as the medical device is advanced through tortuous passageways of the patient's body or may occur after the medical device has reached its targeted destination. The medical device includes a drug agent, for example, carried in or on a hydrophilic or hydrogel coating disposed on the outside thereof. When the hydrogel or drug agent receives an appropriate signal, e.g., solution containing a triggering agent or triggering condition, e.g., heat or light, the hydrogel contracts or expands to squeeze out the drug from hydrogel. If electric current is provided as the signal, and the drug agent is charged, the drug agent is released by electrophoretic forces.

3 Claims, 9 Drawing Sheets

(51) Int. Cl.
*A61N 1/00* (2006.01)
*A61F 2/06* (2013.01)
*A61B 1/012* (2006.01)
*A61N 1/30* (2006.01)
*A61B 1/273* (2006.01)
*A61B 1/31* (2006.01)
*A61B 5/00* (2006.01)
*A61M 25/00* (2006.01)

(56) References Cited

U.S. PATENT DOCUMENTS

| | | |
|---|---|---|
| 3,572,325 A | 3/1971 | Bazell et al. |
| 3,581,738 A | 6/1971 | Moore |
| 4,108,211 A | 8/1978 | Tanaka |
| 4,286,585 A | 9/1981 | Ogawa |
| 4,294,162 A | 10/1981 | Fowler et al. |
| 4,315,309 A | 2/1982 | Coli |
| 4,351,323 A | 9/1982 | Ouchi et al. |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,495,134 A | 1/1985 | Ouchi et al. |
| 4,499,895 A | 2/1985 | Takayama |
| 4,513,235 A | 4/1985 | Acklam et al. |
| 4,515,444 A | 5/1985 | Prescott et al. |
| 4,516,063 A | 5/1985 | Kaye et al. |
| 4,519,391 A | 5/1985 | Murakoshi |
| 4,559,928 A | 12/1985 | Takayama |
| 4,573,450 A | 3/1986 | Arakawa |
| 4,580,210 A | 4/1986 | Nordstrom |
| 4,586,923 A | 5/1986 | Gould et al. |
| 4,615,330 A | 10/1986 | Nagasaki et al. |
| 4,616,630 A | 10/1986 | Arakawa |
| 4,617,915 A | 10/1986 | Arakawa |
| 4,621,618 A | 11/1986 | Omagari et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okabe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoji et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,081,524 A | 1/1992 | Tsuruoka et al. |
| 5,087,989 A | 2/1992 | Igarashi |
| 5,090,959 A * | 2/1992 | Samson et al. ............... 600/116 |
| 5,110,645 A | 5/1992 | Matsumoto et al. |
| 5,111,281 A | 5/1992 | Sekiguchi |
| 5,111,306 A | 5/1992 | Kanno et al. |

(56) References Cited

U.S. PATENT DOCUMENTS

| | | | |
|---|---|---|---|
| 5,111,804 A | 5/1992 | Funakoshi | |
| 5,113,254 A | 5/1992 | Kanno et al. | |
| 5,119,238 A | 6/1992 | Igarashi | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,170,775 A | 12/1992 | Tagami | |
| 5,172,225 A | 12/1992 | Takahashi | |
| 5,174,293 A | 12/1992 | Hagiwara | |
| 5,176,629 A | 1/1993 | Kullas et al. | |
| 5,191,878 A | 3/1993 | Iida et al. | |
| 5,198,931 A | 3/1993 | Igarashi | |
| 5,201,908 A | 4/1993 | Jones | |
| 5,208,702 A | 5/1993 | Shiraiwa | |
| 5,209,220 A | 5/1993 | Hiyama et al. | |
| 5,225,958 A | 7/1993 | Nakamura | |
| 5,228,356 A | 7/1993 | Chuang | |
| 5,236,413 A * | 8/1993 | Feiring | 604/21 |
| 5,243,416 A | 9/1993 | Nakazawa | |
| 5,243,967 A | 9/1993 | Hibino | |
| 5,257,628 A | 11/1993 | Ishiguro et al. | |
| 5,271,381 A | 12/1993 | Ailinger et al. | |
| RE34,504 E | 1/1994 | Uehara et al. | |
| 5,282,785 A * | 2/1994 | Shapland et al. | 604/21 |
| 5,291,010 A | 3/1994 | Tsuji | |
| 5,299,559 A | 4/1994 | Bruce et al. | |
| 5,304,121 A | 4/1994 | Sahatjian | |
| 5,311,858 A | 5/1994 | Adair | |
| 5,325,845 A | 7/1994 | Adair | |
| 5,331,551 A | 7/1994 | Tsuruoka et al. | |
| 5,342,299 A | 8/1994 | Snoke et al. | |
| 5,347,989 A | 9/1994 | Monroe et al. | |
| 5,374,953 A | 12/1994 | Sasaki et al. | |
| 5,379,757 A | 1/1995 | Hiyama et al. | |
| 5,381,782 A | 1/1995 | DeLaRama et al. | |
| 5,390,662 A | 2/1995 | Okada | |
| 5,400,769 A | 3/1995 | Tanii et al. | |
| 5,402,768 A | 4/1995 | Adair | |
| 5,402,769 A | 4/1995 | Tsuji | |
| 5,409,485 A | 4/1995 | Suda | |
| 5,412,478 A | 5/1995 | Ishihara et al. | |
| 5,418,649 A | 5/1995 | Igarashi | |
| 5,420,644 A | 5/1995 | Watanabe | |
| 5,431,645 A | 7/1995 | Smith et al. | |
| 5,434,615 A | 7/1995 | Matumoto | |
| 5,436,640 A | 7/1995 | Reeves | |
| 5,436,767 A | 7/1995 | Suzuki et al. | |
| 5,440,341 A | 8/1995 | Suzuki et al. | |
| 5,464,007 A | 11/1995 | Krauter et al. | |
| 5,469,840 A | 11/1995 | Tanii et al. | |
| 5,473,235 A | 12/1995 | Lance et al. | |
| 5,482,029 A | 1/1996 | Sekiguchi et al. | |
| 5,484,407 A | 1/1996 | Osypka | |
| 5,485,316 A | 1/1996 | Mori et al. | |
| 5,496,260 A | 3/1996 | Krauter et al. | |
| 5,507,296 A | 4/1996 | Bales et al. | |
| 5,515,449 A | 5/1996 | Tsuruoka et al. | |
| 5,518,501 A | 5/1996 | Oneda et al. | |
| 5,524,634 A | 6/1996 | Turkel et al. | |
| 5,543,831 A | 8/1996 | Tsuji et al. | |
| 5,569,158 A | 10/1996 | Suzuki et al. | |
| 5,569,159 A | 10/1996 | Anderson et al. | |
| 5,586,262 A | 12/1996 | Komatsu et al. | |
| 5,589,854 A | 12/1996 | Tsai | |
| 5,591,202 A | 1/1997 | Slater et al. | |
| 5,608,451 A | 3/1997 | Konno et al. | |
| 5,619,380 A | 4/1997 | Ogasawara et al. | |
| 5,622,528 A | 4/1997 | Hamano et al. | |
| 5,631,695 A | 5/1997 | Nakamura et al. | |
| 5,633,203 A | 5/1997 | Adair | |
| 5,643,203 A | 7/1997 | Beiser et al. | |
| 5,645,075 A | 7/1997 | Palmer et al. | |
| 5,647,840 A | 7/1997 | D'Amelio et al. | |
| 5,658,238 A | 8/1997 | Suzuki et al. | |
| 5,666,965 A | 9/1997 | Bales et al. | |
| 5,667,477 A | 9/1997 | Segawa | |
| 5,674,182 A | 10/1997 | Suzuki et al. | |
| 5,674,197 A | 10/1997 | van Muiden et al. | |
| 5,685,823 A | 11/1997 | Ito et al. | |
| 5,685,825 A | 11/1997 | Takase et al. | |
| 5,691,853 A | 11/1997 | Miyano | |
| 5,695,450 A | 12/1997 | Yabe et al. | |
| 5,698,866 A | 12/1997 | Doiron et al. | |
| 5,702,349 A | 12/1997 | Morizumi | |
| 5,703,724 A | 12/1997 | Miyano | |
| 5,704,371 A | 1/1998 | Shepard | |
| 5,704,896 A | 1/1998 | Fukunishi et al. | |
| 5,704,908 A * | 1/1998 | Hofmann et al. | 604/21 |
| 5,707,392 A | 1/1998 | Kortenbach | |
| 5,708,482 A | 1/1998 | Takahashi et al. | |
| 5,721,566 A | 2/1998 | Rosenberg et al. | |
| 5,724,068 A | 3/1998 | Sanchez et al. | |
| 5,728,045 A | 3/1998 | Komi | |
| 5,739,811 A | 4/1998 | Rosenberg et al. | |
| 5,740,801 A | 4/1998 | Branson | |
| 5,746,696 A | 5/1998 | Kondo | |
| 5,764,809 A | 6/1998 | Nomami et al. | |
| 5,767,839 A | 6/1998 | Rosenberg | |
| 5,781,172 A | 7/1998 | Engel et al. | |
| 5,788,714 A | 8/1998 | Ouchi | |
| 5,789,047 A | 8/1998 | Sasaki et al. | |
| 5,793,539 A | 8/1998 | Konno et al. | |
| 5,805,140 A | 9/1998 | Rosenberg et al. | |
| 5,807,306 A * | 9/1998 | Shapland et al. | 604/21 |
| 5,810,715 A | 9/1998 | Moriyama | |
| 5,812,983 A | 9/1998 | Kumagai | |
| 5,819,736 A | 10/1998 | Avny et al. | |
| 5,820,591 A | 10/1998 | Thompson et al. | |
| 5,821,466 A | 10/1998 | Clark et al. | |
| 5,821,920 A | 10/1998 | Rosenberg et al. | |
| 5,823,948 A | 10/1998 | Ross, Jr. et al. | |
| 5,827,186 A | 10/1998 | Chen et al. | |
| 5,827,190 A | 10/1998 | Palcic et al. | |
| 5,828,197 A | 10/1998 | Martin et al. | |
| 5,828,363 A | 10/1998 | Yaniger et al. | |
| 5,830,124 A | 11/1998 | Suzuki et al. | |
| 5,830,128 A | 11/1998 | Tanaka | |
| 5,836,869 A | 11/1998 | Kudo et al. | |
| 5,837,023 A | 11/1998 | Koike et al. | |
| 5,840,014 A | 11/1998 | Miyano et al. | |
| 5,841,126 A | 11/1998 | Fossum et al. | |
| 5,843,000 A | 12/1998 | Nishioka et al. | |
| 5,843,016 A | 12/1998 | Lugnani et al. | |
| 5,846,183 A | 12/1998 | Chilcoat | |
| 5,855,560 A | 1/1999 | Idaomi et al. | |
| 5,857,963 A | 1/1999 | Pelchy et al. | |
| 5,865,724 A | 2/1999 | Palmer et al. | |
| 5,868,664 A | 2/1999 | Speier et al. | |
| 5,868,666 A | 2/1999 | Okada et al. | |
| 5,873,816 A | 2/1999 | Kagawa et al. | |
| 5,873,866 A | 2/1999 | Kondo et al. | |
| 5,876,326 A | 3/1999 | Takamura et al. | |
| 5,876,331 A | 3/1999 | Wu et al. | |
| 5,876,373 A | 3/1999 | Giba et al. | |
| 5,876,427 A | 3/1999 | Chen et al. | |
| 5,877,819 A | 3/1999 | Branson | |
| 5,879,284 A | 3/1999 | Tsujita | |
| 5,880,714 A | 3/1999 | Rosenberg et al. | |
| 5,882,293 A | 3/1999 | Ouchi | |
| 5,882,339 A | 3/1999 | Beiser et al. | |
| 5,889,670 A | 3/1999 | Schuler et al. | |
| 5,889,672 A | 3/1999 | Schuler et al. | |
| 5,892,630 A | 4/1999 | Broome | |
| 5,895,350 A | 4/1999 | Hori | |
| 5,897,507 A | 4/1999 | Kortenbach et al. | |
| 5,897,525 A | 4/1999 | Dey et al. | |
| 5,907,487 A | 5/1999 | Rosenberg et al. | |
| 5,916,175 A | 6/1999 | Bauer | |
| 5,923,018 A | 7/1999 | Kameda et al. | |
| 5,928,136 A | 7/1999 | Barry | |
| 5,929,607 A | 7/1999 | Rosenberg et al. | |
| 5,929,846 A | 7/1999 | Rosenberg et al. | |
| 5,929,900 A | 7/1999 | Yamanaka | |

(56) References Cited

U.S. PATENT DOCUMENTS

| | | | |
|---|---|---|---|
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,951,489 A | 9/1999 | Bauer |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,001,088 A * | 12/1999 | Roberts et al. ........... 604/501 |
| 6,002,425 A | 12/1999 | Yamanaka et al. |
| 6,007,531 A | 12/1999 | Snoke et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,022,319 A * | 2/2000 | Willard et al. ........... 600/470 |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,100,874 A | 8/2000 | Schena et al. |
| 6,104,382 A | 8/2000 | Martin et al. |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamura |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,241,668 B1 | 6/2001 | Herzog |
| 6,260,994 B1 | 7/2001 | Matsumoto et al. |
| 6,264,617 B1 | 7/2001 | Bales et al. |
| 6,272,470 B1 | 8/2001 | Teshima |
| 6,275,255 B1 | 8/2001 | Adair et al. |
| 6,280,411 B1 * | 8/2001 | Lennox ............... 604/103.05 |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,309,375 B1 | 10/2001 | Glines et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,366,799 B1 | 4/2002 | Acker et al. |
| 6,381,029 B1 | 4/2002 | Tipirneni |
| 6,398,724 B1 | 6/2002 | May et al. |
| 6,409,716 B1 | 6/2002 | Sahatjian et al. |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,489,987 B1 | 12/2002 | Higuchi et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,520,908 B1 | 2/2003 | Ikeda et al. |
| 6,524,234 B2 | 2/2003 | Ouchi |
| 6,527,759 B1 * | 3/2003 | Tachibana et al. ......... 604/500 |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,558,317 B2 | 5/2003 | Takahashi et al. |
| 6,561,971 B1 | 5/2003 | Akiba |
| 6,565,507 B2 | 5/2003 | Kamata et al. |
| 6,569,105 B1 | 5/2003 | Kortenbach et al. |
| 6,574,629 B1 | 6/2003 | Cooke, Jr. et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,671,561 B1 | 12/2003 | Moaddeb |
| 6,673,012 B2 | 1/2004 | Fujii et al. |
| 6,677,984 B2 | 1/2004 | Kobayashi et al. |

(56) References Cited

U.S. PATENT DOCUMENTS

| | | | |
|---|---|---|---|
| 6,678,397 B1 | 1/2004 | Ohmori et al. |
| 6,682,479 B1 | 1/2004 | Takahashi et al. |
| 6,685,631 B2 | 2/2004 | Minami |
| 6,686,949 B2 | 2/2004 | Kobayashi et al. |
| 6,690,409 B1 | 2/2004 | Takahashi |
| 6,690,963 B2 | 2/2004 | Ben-Haim et al. |
| 6,692,430 B2* | 2/2004 | Adler | 600/109 |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B2 | 3/2004 | Benaron et al. |
| 6,715,068 B1 | 3/2004 | Abe |
| 6,716,162 B2 | 4/2004 | Hakamata |
| 6,728,599 B2 | 4/2004 | Wang et al. |
| 6,730,018 B2 | 5/2004 | Takase |
| 6,736,773 B2 | 5/2004 | Wendlandt et al. |
| 6,743,240 B2 | 6/2004 | Smith et al. |
| 6,749,559 B1 | 6/2004 | Kraas et al. |
| 6,749,560 B1 | 6/2004 | Konstorum et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami |
| 6,949,068 B2 | 9/2005 | Taniguchi et al. |
| 6,950,691 B2 | 9/2005 | Uchikubo |
| 6,955,671 B2 | 10/2005 | Uchikubo |
| 6,962,564 B2 | 11/2005 | Hickle |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0032863 A1 | 2/2003 | Kazakevich |
| 2003/0069897 A1 | 4/2003 | Roy et al. |
| 2003/0073928 A1 | 4/2003 | Kortenbach et al. |
| 2003/0097042 A1 | 5/2003 | Eino |
| 2003/0149338 A1 | 8/2003 | Francois et al. |
| 2003/0181905 A1 | 9/2003 | Long |
| 2003/0229384 A1* | 12/2003 | Mon | 607/96 |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0183010 A1 | 9/2004 | Reilly et al. |
| 2004/0249247 A1 | 12/2004 | Iddan |
| 2004/0257608 A1 | 12/2004 | Tipirneni |
| 2005/0075538 A1 | 4/2005 | Banik et al. |
| 2005/0197536 A1 | 9/2005 | Banik et al. |
| 2005/0197861 A1 | 9/2005 | Omori et al. |
| 2005/0203341 A1 | 9/2005 | Welker et al. |
| 2005/0228697 A1 | 10/2005 | Funahashi |
| 2006/0030936 A1* | 2/2006 | Weber et al. | 623/1.42 |
| 2006/0193893 A1* | 8/2006 | Brown | 424/426 |

FOREIGN PATENT DOCUMENTS

| | | |
|---|---|---|
| JP | 58-78635 A | 5/1983 |
| JP | 05-31071 A | 2/1993 |
| JP | 05-091972 A | 4/1993 |
| JP | 06-105800 A | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A2 | 4/2002 |
| JP | 2002-177197 A2 | 6/2002 |
| JP | 2002-185873 A2 | 6/2002 |
| JP | 2002-253481 A2 | 9/2002 |
| JP | 3377273 B2 | 11/2002 |
| JP | 2003-075113 A2 | 3/2003 |
| JP | 3482238 A2 | 10/2003 |
| WO | WO 93/13704 A1 | 7/1993 |
| WO | 9604955 A | 2/1996 |
| WO | 9736632 A | 10/1997 |

(56) References Cited

FOREIGN PATENT DOCUMENTS

| | | |
|---|---|---|
| WO | 9828364 A | 7/1998 |
| WO | WO 2004/016310 A2 | 2/2004 |
| WO | WO 2005/023082 A2 | 3/2005 |

OTHER PUBLICATIONS

Murdan, S., "Electro-Responsive Drug Delivery From Hydrogels," *Journal of Controlled Release 92*:1-17, 2003.

* cited by examiner

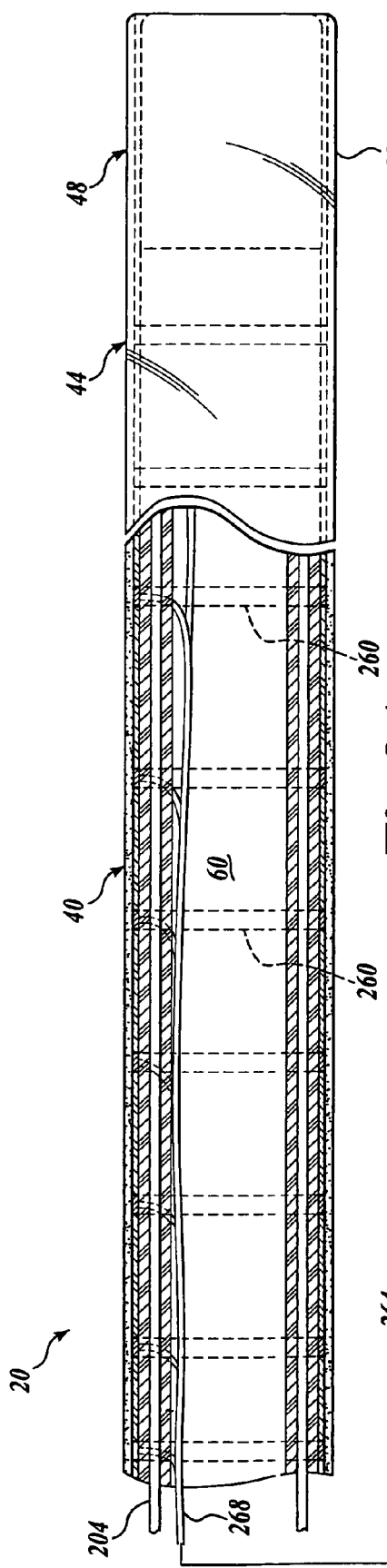
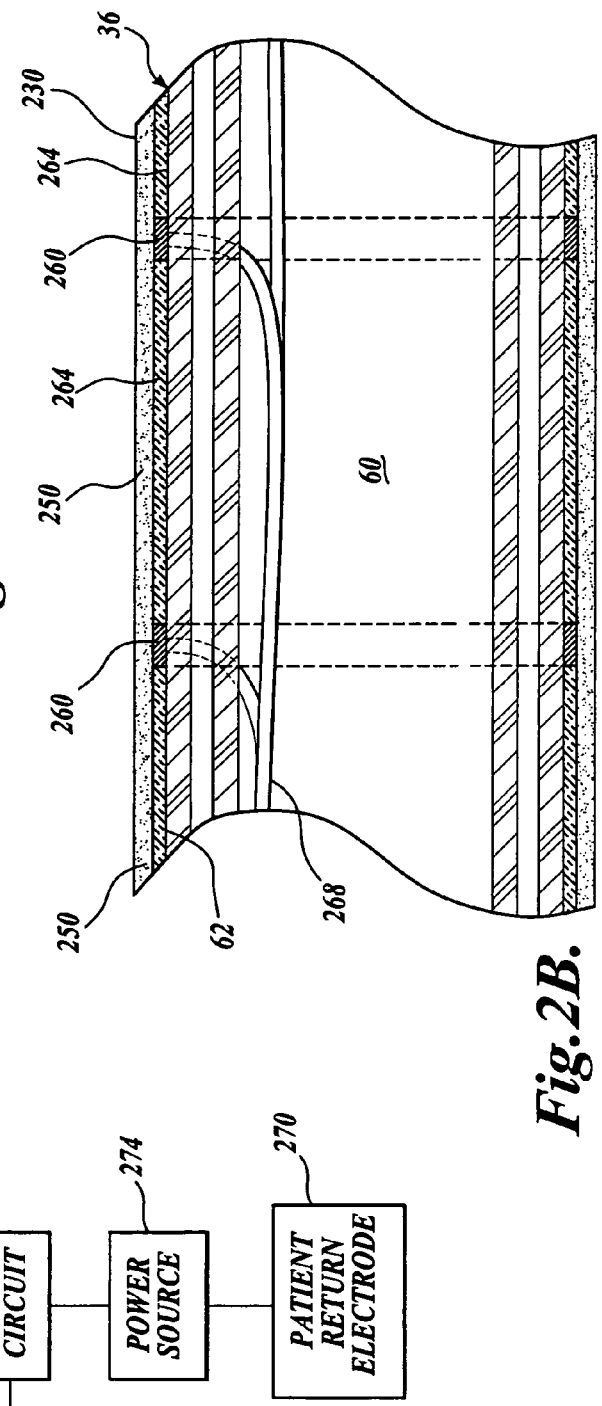
Fig.2A.
Fig.2B.

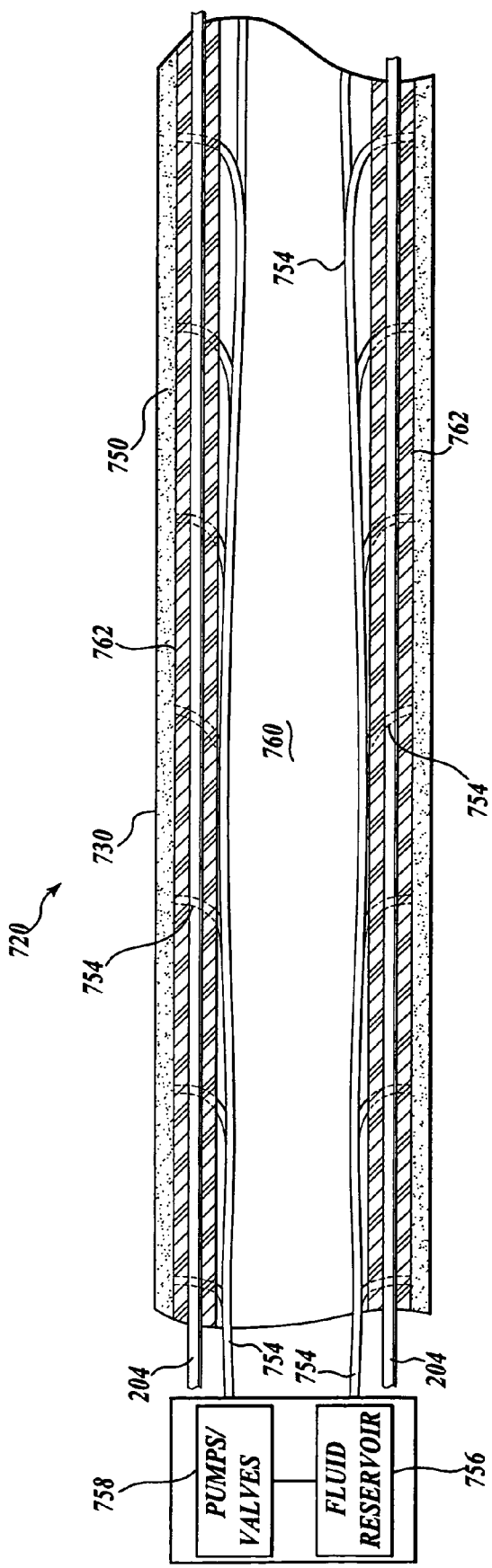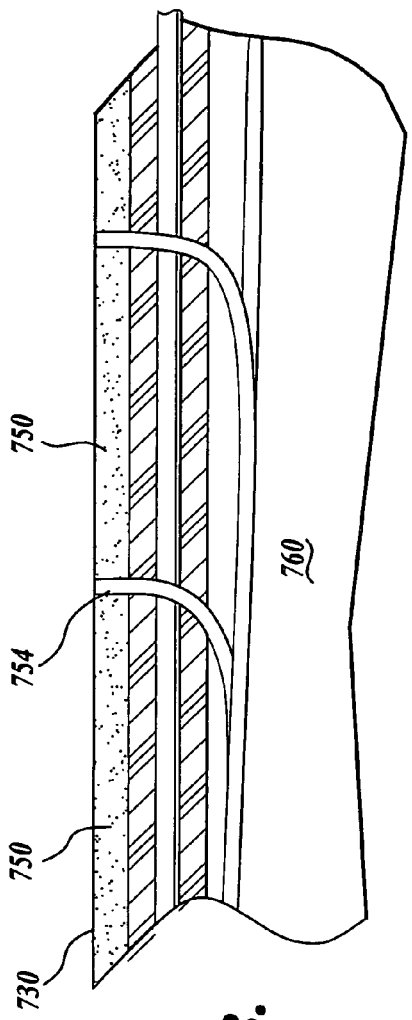
Fig. 8A.
Fig. 8B.

MEDICAL DEVICES WITH LOCAL DRUG DELIVERY CAPABILITIES

FIELD OF THE INVENTION

The present invention is directed to devices suitable for use in medical procedures and, more particularly, to medical devices such as endoscopes, catheters, or the like, that include local drug delivery capabilities.

BACKGROUND OF THE INVENTION

An endoscope is a piece of surgical equipment that has imaging capabilities so as to be able to provide images of an internal body cavity of a patient. Most minimally invasive surgical procedures performed in the gastrointestinal (GI) tract or other internal body cavities are accomplished with the aid of an endoscope.

Endoscopes are essentially formed by a flexible shaft that is introduced into the GI tract after being inserted in the body cavity, starting from the anus or from the mouth of a subject. The endoscope typically includes a steerable tip to facilitate navigation of the endoscope through the GI tract, and is typically of sufficient stiffness so that it can be advanced along the body cavity without buckling. The tip of the endoscope that is introduced in the GI tract can be outfitted with several devices, most notably an illumination device and a vision device, such as a vision integrated circuit, so that the operator of the endoscope can examine the interior of the GI tract and maneuver the tip of the endoscope into the proper position.

Endoscopes are typically utilized in extremely tortuous passageways, such as the GI tract, which requires the endoscope to be advanced by pushing on the proximal end of the scope while steering the tip inside the passageway, the endoscope thereby exerting pressure against the walls of the passageway. Such advancing techniques, in conjunction with the configuration of the endoscope and the GI tract, can result in localized patient discomfort or pain as the endoscope is pressed against the lumen wall during manipulation. At times when the endoscope is advanced, "looping" occurs, a condition where the endoscope forms a coiled shape when inserted. The loop may cause the side of the endoscope to press against the lumen wall, for example, the intestine, and distend the intestinal wall instead of advancing along the intestine. In conventional endoscope systems, patient discomfort is reduced in patients undergoing endoscopic GI procedures through the use of sedation. However, there are risks associated with the use of sedatives. Therefore, a need exists to provide localized anesthesia to a patient undergoing an endoscopic procedure.

SUMMARY OF THE INVENTION

Embodiments of the present invention are directed to medical devices and, in particular, to endoscopes that reduce or eliminate the need for sedation in a patient by providing localized drug delivery. By administering drugs such as sedative drug agents locally at the region of pain or discomfort during an endoscopic procedure, the overall amount of drugs administered to the patient is lowered, thereby reducing the potential risks inherent in administering sedatives to a patient. Embodiments of the present invention may also be used to deliver other types of drug agents via an endoscope, such as therapeutic drug agents.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 2A is a partial longitudinal cross-sectional view of the endoscope shown in FIG. 1;

FIG. 2B is a magnified partial longitudinal cross-sectional view of the endoscope shown in FIG. 2A;

FIG. 8A is a partial longitudinal cross-sectional view of another embodiment of an endoscope formed in accordance with aspects of the present invention; and FIG. 8B is a magnified partial longitudinal cross-sectional view of another embodiment of an endoscope formed in accordance with aspects of the present invention;

DETAILED DESCRIPTION OF EXEMPLARY EMBODIMENTS

Embodiments of the present invention will now be described with reference to the drawings, where like numerals correspond to like elements. Embodiments of the present invention are directed to devices of the type broadly applicable to numerous medical applications in which it is desirable to insert an imaging device, catheter, or similar device into a body lumen or passageway. Specifically, embodiments of the present invention are directed to medical devices having local, targeted drug delivery capabilities. Several embodiments of the present invention are directed to medical devices having local drug delivery capabilities that incorporate endoscopic features, such as illumination and visualization capabilities, for endoscopically viewing anatomical structures within the body. As such, embodiments of the present invention can be used for a variety of different diagnostic and interventional procedures including colonoscopy, upper endoscopy, bronchoscopy, thoracoscopy, laparoscopy, and video endoscopy, etc., and are particularly well suited for negotiating tortuous passageways of the patient's body.

Although exemplary embodiments of the present invention will be described hereinafter as endoscopes, it will be appreciated that aspects of the present invention have wide application and may be incorporated into other medical devices such as catheters, where local, targeted drug delivery is desirable. Accordingly, the following descriptions and illustrations herein should be considered illustrative in nature and, thus, not limiting the scope of the present invention as claimed.

Figure 1:
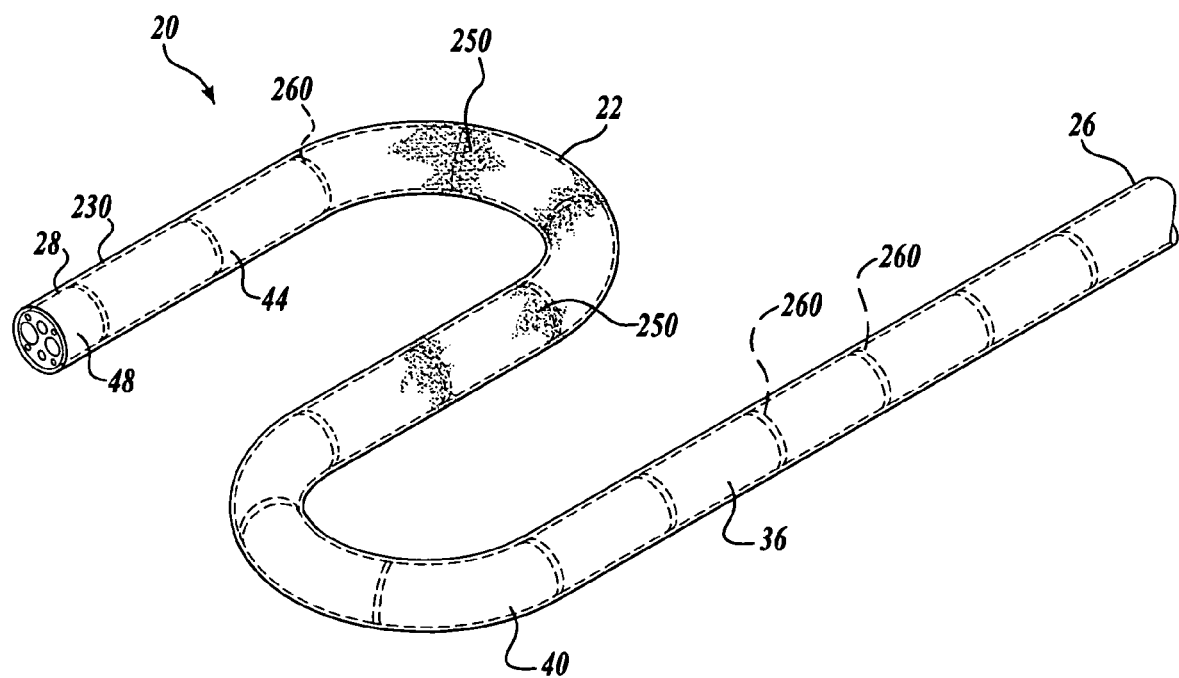
FIG. 1 is a perspective view of one embodiment of a medical device, in particular, an endoscope constructed in accordance with aspects of the present invention.

FIG. 1 illustrates one exemplary embodiment of a medical device and, in particular, an endoscope 20 constructed in accordance with aspects of the present invention. The endoscope 20 has a proximal end 26 and a distal end 28. The proximal end 26 may be functionally connected to a control console (not shown) that operates the endoscope 20. The endoscope 20 includes an elongated shaft-like body 36 comprised of a proximal shaft section 40, an optional articulation section 44, and a tip section 48 disposed at the distal end 28 of the endoscope 20.

In one embodiment, the endoscope 20 is at least partially covered with an outer layer 230 along its shaft-like body 36. The outer layer 230 may cover the entire endoscope 20 or any selected portion or portions thereof. In one embodiment, the outer layer 230 has a lubricious outer surface constructed of a hydrophilic material that allows the endoscope 20 to be advanced more easily through the passageways of the patient. In one embodiment, the outer layer 230 includes localized drug delivery capabilities for selectively delivering at least one drug in vivo, such as when the endoscope is advanced through the tortuous passageways of the patient's body, as described in more detail below.

Referring now to FIGS. 2A-2B, the proximal shaft section 40 comprises an elongated tubular construction having an axial, centralized lumen 60 and an outer surface 62. The centralized lumen 60 is sized to allow for endoscope components, such as optics, working devices, fluid channels, and the like, to be routed to the tip section 48 of the endoscope 20. Additionally, the centralized lumen 60 allows for the passage of electrical wires or fluid delivery tubes, as will be described in more detail below. The proximal shaft section 40 is flexible, i.e., bendable, but substantially non-compressible (e.g., non-kinkable) along its length. The proximal shaft section 40 may be of any suitable construction and made of any suitable material. In one embodiment, the proximal shaft section 40 may be made of a polymeric material such as a polyurethane, polyimide, PTFE, polyethylene, or a high strength thermoplastic elastomer, such as a polyether bock amide (Pebax®) or the like, and combinations thereof. If desired, the proximal shaft section 40 may be reinforced along its length to increase its torsional stiffness. For example, the shaft section 40 may include wire reinforcements as described in copending U.S. patent application Ser. No. 10/811,781, filed Mar. 29, 2004, and U.S. patent application Ser. No. 10/956,007, entitled "Video Endoscope," filed Sep. 30, 2004, the disclosures of which are hereby incorporated by reference.

At the distal region of the endoscope 20 adjacent the distal end of the proximal section 40 is an optional articulation section 44, as best shown in FIG. 1. The articulation section 44, in use, allows the distal end 28 to be selectively steered, manipulated, or bent in one or more planes by action occurring at the proximal end of the endoscope 20. The articulation section 44 may allow the tip section 48 to be turned back on itself, i.e., over an arc of up to 180 degrees, and can be directed to bend in any direction desired about the circumference of the distal tip section. That is, the operator can select both the amount of the bend or articulation and the direction of the bend. For several non-limiting examples of articulation sections that may be practiced with the present invention, please see copending U.S. patent application Ser. No. 10/811,781, filed Mar. 29, 2004, U.S. Pat. No. 5,846,183, and U.S. patent application Ser. No. 10/956,007, entitled "Video Endoscope," filed Sep. 30, 2004, the disclosures of which are hereby incorporated by reference.

Figure 3:
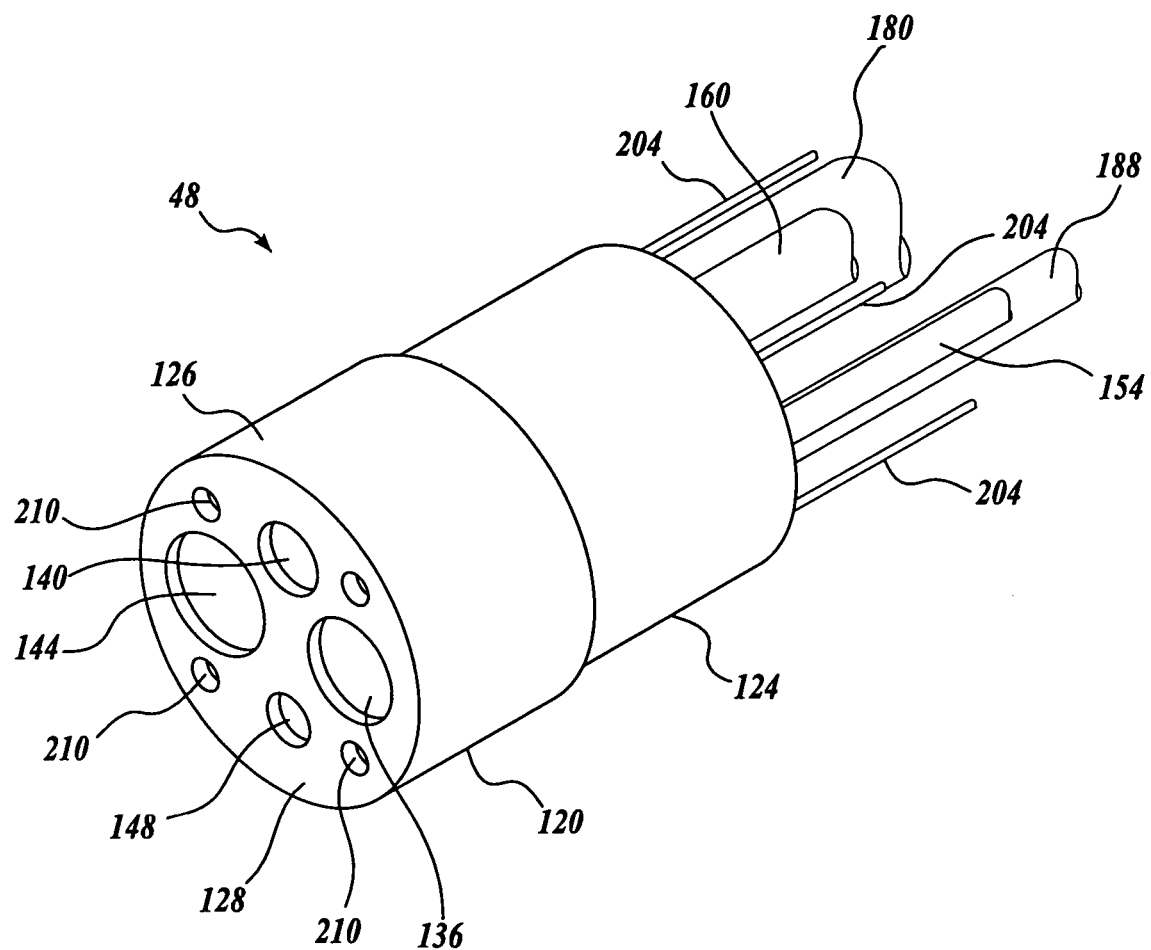
FIG. 3 is a partial perspective view of one embodiment of a distal tip section of the endoscope of FIG. 1.

Returning to FIG. 1, the body of the endoscope 20 includes a tip section 48 that is connected to the distal end of the articulation section 44. FIG. 3 illustrates one embodiment of a tip section 48 that comprises a cylindrical body having a distal section 120 and a proximal section 124. The tip section 48 is preferably made of a biocompatible plastic of which many examples have been described hereinabove. As will be described in detail below, the distal section 120 defines side surfaces 126 to which light sources may be mounted. The distal face 128 of the distal tip section 48 includes a number of ports including an imaging device port 136, one or more illumination ports 140, an access port 144 for a working channel lumen, and an insufflation/irrigation port 148.

As best shown in FIG. 3, an image sensor (not shown) that preferably comprises a charged coupled device (CCD), CMOS imaging sensor, or other solid state imaging device and one or more glass or polymeric lenses that produce electronic signals representative of an image of the scene in front of the imaging device port 136 is fitted within the imaging device port 136. The signals may be routed to a video processing and display device at the proximal end of the endoscope through transmission cabling 154 that is routed through the centralized lumen of the endoscope. The image sensor is preferably a low noise, CMOS color imager such as VGA, SVGA, SXGA, or XGA. If less resolution is desired, a ½ VGA sensor could also be used. For conventional video systems, a minimum frame rate of 25 to 30 fps is required to achieve real-time video. The video output of the system may be in any digital or analog format, including conventional formats such as PAL or NTSC, or high definition video format.

The illumination port 140 houses one or more lenses at the distal end of a fiber optic bundle 160. The fiber optic bundle 160 is routed through the centralized lumen from the proximal end 26 to the distal end 28 of the endoscope 20. The fiber optic bundle 160 transmits light generated at the proximal end of the endoscope by, for example, a laser or high intensity lamp source, to the distal end of the endoscope where it is emitted from the illumination port 140. Alternatively, the illumination ports 140 house one or more light emitting diodes (LEDs) that are not shown for ease of illustration. The LEDs may be high intensity white light sources or may comprise colored light sources such as infrared (IR), visible lights, e.g., red, green, blue, or ultra-violet (UV) LEDs. With colored LEDs, images in different spectral bands may be obtained due to illumination with any one or more individual colors. White light images may be obtained by the simultaneous or sequential illumination of the colored LEDs and combining individual color images at each illumination wavelength. If sequential illumination of colored LEDs is employed, as an alternative, a monochrome CMOS imager can be used.

The access port 144 is the termination point of a working channel 180 of the endoscope 20 that extends from outside the proximal end of the endoscope 20 to the distal end through the centralized lumen of the endoscope. The working channel 180 is defined by a sheath that is non-collapsible (e.g., non-kinkable) and thus tends to maintain a circular cross section even when it is bent along its axis. The working channel 180 can also include a reinforcement coil to help maintain its cross-sectional shape. The working channel 180 tends to retain a constant size when the sheath is used so that binding of the tools inserted in the working channel 180 is prevented and the cross-sectional shape is resistant to collapse during suction.

The flush port 148 is connected in fluid communication with an irrigation and insufflation lumen 188 for discharging liquid and air from the distal face 128 of the distal tip section 48. In one embodiment, the liquid and air are preferably discharged from the flush port 148 in the direction of the imaging device port 136 and/or the illumination ports 140. The irrigation/insufflation lumen 188 is routed from the proximal end 28 of the endoscope to the distal tip section 48 through the centralized lumen of the endoscope. The proximal end of the irrigation/insufflation lumen 188 is adapted for connection to a source of irrigation/insufflation fluids disposed externally from the endoscope. It will be appreciated that the irrigation/insufflation lumen 188 may alternatively be two separate lumens, thus necessitating two flush ports.

Referring now to FIG. 2A, steering of the distal end 28 of the endoscope 20 can be carried out in a convenient manner by using a plurality of control cables 204 that extend longitudinally through the endoscope 20 from the proximal end and terminate at or near the distal end of the endoscope 20.

As shown in FIG. 2B, the endoscope 20 may be at least partially covered with an outer layer 230 along its shaft-like body 36 for providing the endoscope 20 with a friction-reducing outer surface. The outer layer 230 preferably comprises a hydrophilic material that is biocompatible and capable of carrying drug agents by absorption, chemical bonding, e.g., ionic, covalent, and/or by other conventional techniques, as will be described below. In some embodiments of the present invention, the hydrophilic material is a lubricious coating constructed from a hydrophilic polymer that allows selective release of one or more drug agents disposed therein. Hydrophilic polymers suitable for use as hydrophilic lubricous coatings, such as polyacrylamide, are known in the art. In other embodiments, the layer 230 comprises a hydrogel coating that is composed largely of water molecules, such as polyuronic acid or other polymeric hydrogel coatings. The outer layer 230 may additionally contain other hydrophilic polymers and other lubricious ingredients in addition to the hydrophilic polymer hydrogel. The outer layer 230 may be attached to the outer surface 62 of the shaft-like body 36 using any art-recognized method. For example, the outer layer 230 may be attached through the reaction of organic functional groups on the hydrophilic polymers with a crosslinking agent contained in the catheter body. As another example, the outer surface of the shaft-like body may be treated to allow covalent attachment of the layer 230.

In accordance with one aspect of the present invention, the endoscope 20 further includes local drug delivery capabilities that allow selective administration of a drug agent in vivo. In some applications, selective release of drug agents such as analgesic or sedative agents is initiated via a user input signal to allow for drug agent release in a specific location where the patient is feeling some discomfort as the endoscope 20 is routed through the patient's body. In one embodiment, the endoscope 20 utilizes electrophoretic forces to selectively release the drug agent from the endoscope during use. As will be described in greater detail below, embodiments of the present invention may include other drug release signals or stimuli such as light, heat (i.e., thermal), chemical, acoustic, etc., for selectively releasing the drug agent from the endoscope in vivo.

Referring now to FIGS. 2A-2B, there is shown a longitudinal cross-sectional view of one embodiment of the endoscope 20 having local drug delivery capabilities that utilize electrophoresis to selectively administer the drug agent at chosen locations. As best shown in FIG. 2B, a drug agent 250 is carried by, impregnated, or otherwise disposed in or on the outer layer 230.

Figure 2C:
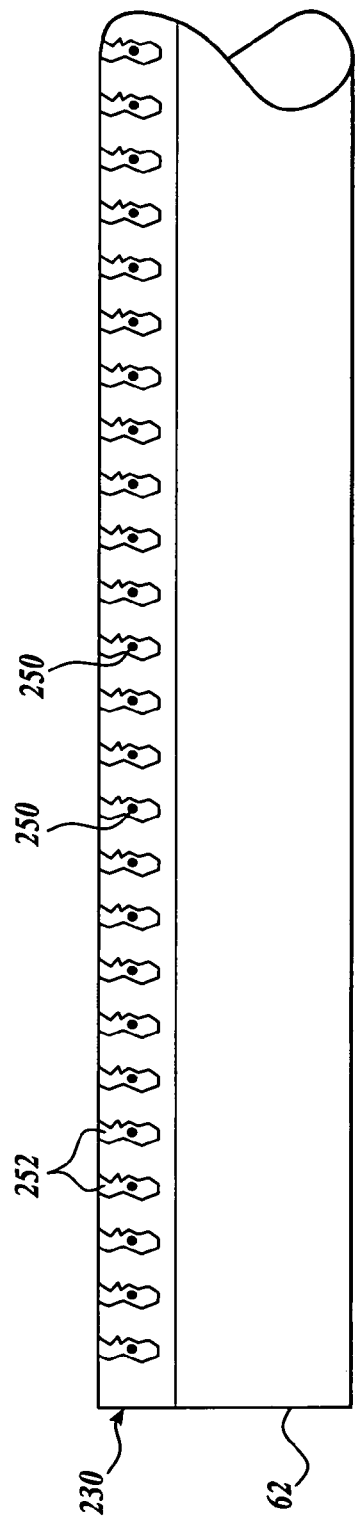
FIG. 2C is a magnified partial longitudinal cross-sectional view of the endoscope shown in FIG. 2A having an outer layer comprising a porous structure including one or more drug agents, in accordance with an embodiment of the present invention.

FIG. 2C is a longitudinal cross-sectional view of the shaft 36 shown in FIG. 2A, illustrating an embodiment of the outer layer 230 comprising a porous structure including a plurality of nanopores 252 having drug agents 250 disposed therein.

Figure 2D:
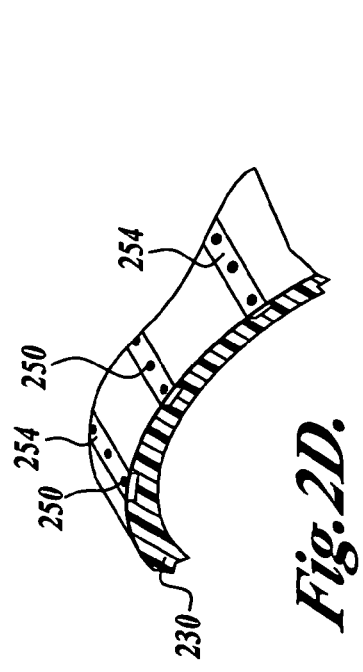
FIG. 2D is a cross-sectional view of the endoscope shown in FIG. 2A having an outer layer comprising a plurality of microchannels including one or more drug agents, in accordance with an embodiment of the present invention.

FIG. 2D is a cross-sectional view of the shaft 36 shown in FIG. 2A, illustrating an embodiment of the outer layer 230 comprising a plurality of microchannels 254 having drug agents 250 disposed therein. The microchannels 254 may be oriented in any direction.

Figure 2E:
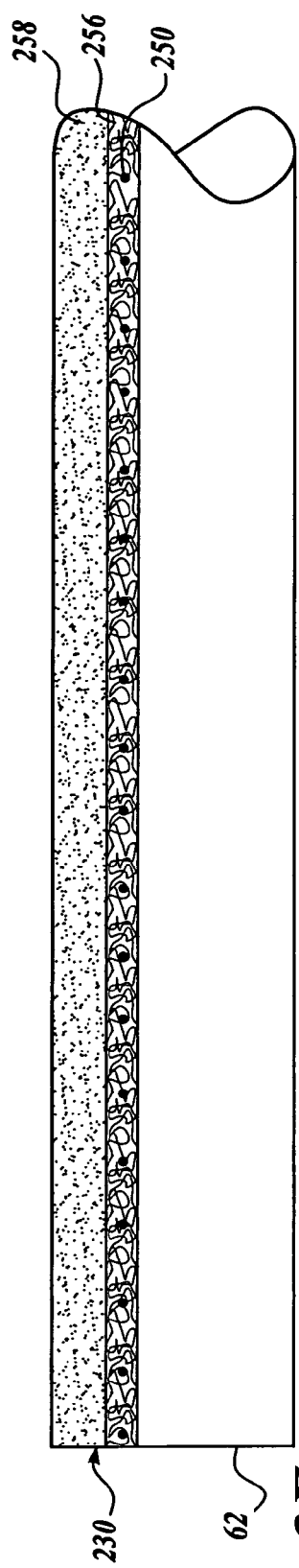
FIG. 2E is a magnified partial longitudinal cross-sectional view of the endoscope shown in FIG. 2A having an outer layer comprising a porous layer comprising one or more drug agents covered with a hydrogel layer, in accordance with an embodiment of the present invention.

FIG. 2E is a partial longitudinal cross-sectional view of the shaft 36 shown in FIG. 2A illustrating an embodiment of the layer 230 comprising a first porous region 256 having one or more drug agents 250 embedded therein, and a second hydrophilic region 258 at least partially covering the first porous region 256. The hydrophilic region 258 may comprise a hydrophilic material such as hydrogel. The drug agent 250 may also be disposed within the hydrophilic region 258.

In one embodiment, the one or more drug agents 250 is delivered locally to the patient through the outer layer 230. In such embodiments, the one or more drug agents 250 is preferably charged molecules that are delivered locally to the patient via electrophoresis. In one embodiment, the outer layer 230 is a hydrogel such as a polyacrylamide hydrogel and the drug agent 250 is an analgesic or sedative agent having an electric charge, which is capable of being released from the hydrogel outer layer through electrophoresis. Any suitable analgesic or sedative drug agents 250 having an electric charge may be used in accordance with an embodiment of the shaft 36. For example, procaine, lidocaine-HCL, benzocaine, cocaine, bupivacaine, ropivacaine, prilocalne, and mepicaine chloroprocaine, or polar derivatives thereof, may be used in accordance with various embodiments of the invention.

Other neutral charged analgesics or sedative agents, as well as other drug agents, for example, therapy drug agents (e.g., anti-inflammatory, antibiotics, etc.), may also be used if combined with a charged carrier. For example, a neutral or a weakly charged drug agent can also be used if it can be converted to a charged moiety. There are a variety of ways for carrying out such a conversion, as known in the art. For instance, one typical method includes forming an emulsion of the drug or drug particle with a surfactant. Examples of surfactants that can be used are, without limitation, fatty acids, phospholipids, and sodium acetyl sulfate. In another known method, the drug agent can be converted to a charged moiety by cyclodextrin encapsulation.

The drug agent 250 may be uniformly or non-uniformly dispersed in or on the outer layer 230. For example, the concentration of the drug agent may be constant along the length of the endoscope or may have greater or lesser concentrations along the length, including gaps where little or no drug agent is present. Additionally, the concentration of the drug agent around the circumference of the endoscope may have either constant or varying concentrations, including little or no drug agent being present. Further, the concentration of the drug agent may be constant or non-constant throughout the thickness of the outer layer 230. In some embodiments, the drug agent 250 may be attached as a surface layer to a portion of the endoscope surface having an electron charge. For example, the drug agent 250 may be attached as a surface deposit in any suitable configuration, such as in one or more channels or in a spiral pattern.

The endoscope 20 further includes a drug release control that signals the release of the drug agent 250 from the outer layer 230. The drug release control may be specifically selected based on the drug to be delivered and/or the outer layer to be used. In one embodiment, the endoscope 20 utilizes electromotive forces to selectively release the drug agent from the outer layer 230 by electrophoresis, as will now be described in more detail. In the embodiment shown in FIGS. 2A-2B, the drug release control of the endoscope 20 includes a plurality of electrodes 260 disposed in between the outer surface 62 of the shaft-like body 36 and the inner surface of the layer 230. Alternatively, the electrodes 260 may be suspended or imbedded in the outer layer 230. The electrodes 260 may be selectively arranged along the length of the endoscope and around the circumference of the endoscope proximate the disposed drug agent 250, as desired. In the embodiment of the present invention illustrated in FIGS. 2A-2B, the electrodes 260 are in the form of rings and arranged in an array. The spacing between the electrodes 260 along the shaft may be constant or may vary, depending on the application.

The electrodes 260 may be electrically isolated from one another via insulators 264. The insulators 264 may be formed from ceramic, glass, glass-ceramic, polytetrafluoroethylene (PTFE), polyimide, or a number of other materials that are non-conductive and biocompatible. In one embodiment, the electrodes 260 are preferably made of copper or gold and affixed to the shaft-like body via vapor deposition or other techniques known in the art. It will be appreciated that the insulators and/or the electrodes may include radiopaque materials or markers so that the endoscope may be viewed fluoroscopically during use. Materials that may be included as conductors are gold, platinum, silver, tungsten, barium sulfide, and bismuth oxide. Examples of radiopaque materials that may be included in the electrodes include, but are not limited to, gold and platinum.

Each electrode 260 is electrically connected to a power source 274, such as an electronic circuit or a simple battery, located at the proximal end of the endoscope or external to the endoscope. In exemplary embodiments, the power source 274 is preferably a low voltage source capable of outputting approximately 3-10 volts. In one embodiment, the power source 274 is a nine (9) volt battery. To electrically connect the electrodes 260 to the power source 274, electrical wires 268, such as copper wires protected in plastic sheaths, may be used. The electrical wires may be disposed along the outer surface 62 or may be routed through the lumen 60 of the endoscope body and through access openings positioned in the endoscope body walls adjacent the electrodes. Alternatively, the electrical wires may be routed through lumens formed in the shaft walls.

As best shown in FIGS. 2A-2B, the electrodes 260 and the power source 274 are configured in a monopolar design. As such, to complete the circuit, a patient return or reference electrode 270 is provided. The patient return or reference electrode 270 is electrically connected to the power source 274. During use, the patient return or reference electrode 270 is connected to the patient, preferably to the exterior of the patient remote from the endoscope. In the embodiment shown, a switch circuit 264 having multiple nodes is connected in between the electrodes 260, 270 and the power source 274 in a conventional manner so that each electrode 260 may be selectively energized one at a time through activation of the switch circuit. It will be appreciated that the switching circuit may be activated by user input or may be programmed to activate according to specific parameters, such as time, images captured by the endoscope, etc.

It will be appreciated that other electrical circuitry, such as multiplexers, may be used to reduce the number of wires 268. Alternatively, the electrodes 260 may be mounted to a flex circuit (not shown) in a conventional manner. The flex circuit may be in the form of sheaths or strips to which power is received from the power source 274 in a conventional manner.

The operation of one exemplary embodiment of the endoscope 20 for selectively releasing or administering a drug agent will now be described with reference to FIGS. 1 and 2A-2B. To use the endoscope 20 in a medical procedure, the distal tip section 48 is inserted into a body opening, such as the anus or the mouth. The endoscope 20 is then advanced through the selected passageways in a conventional manner. As the endoscope 20 is advanced, the distal tip section 48 may be controllably steered using the control wires 204 to navigate the tortuous passageways of the patient.

During the surgical procedure, the endoscope 20 may create discomfort to the patient as the endoscope is steered and advanced around the tortuous passageways. Prior to, during, or after patient discomfort, the physician may administer a localized analgesic at the area of discomfort by activating the drug release control, which signals the release of the drug agent 250 from the outer layer 230. In this particular embodiment, the physician administers the drug agent 250 by selectively sending power to one or more of the electrodes 260. As power travels between the electrodes 260 and 270, the drug agent 250 is forced out of the outer layer 230 and into the patient lumen and surrounding tissue by electrophoresis.

Figure 4:
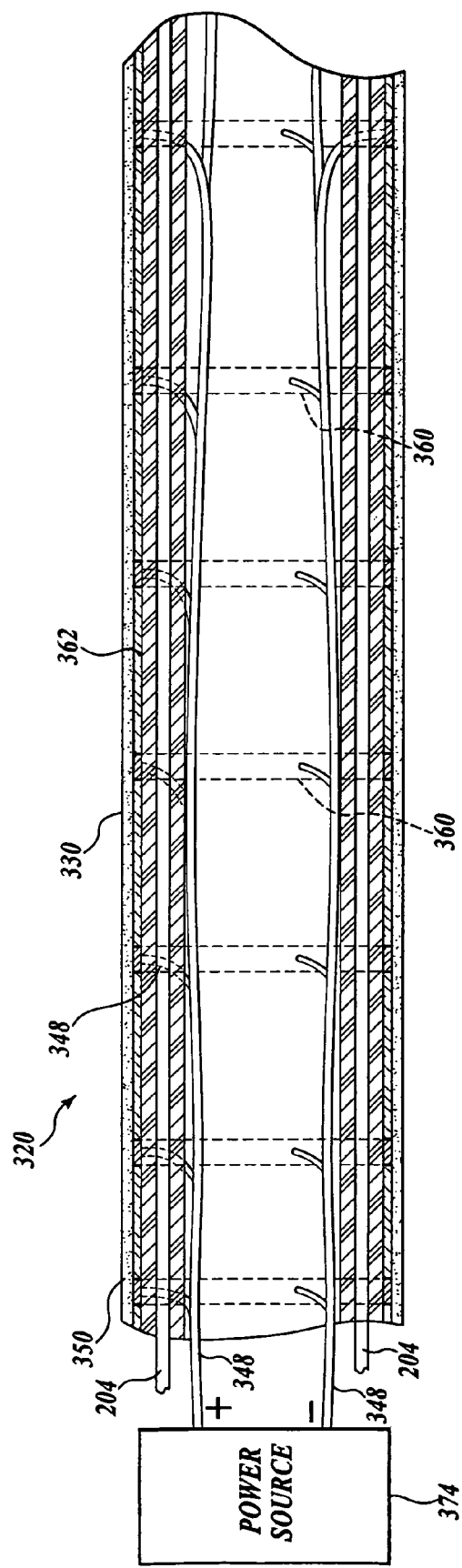
FIG. 4 is a partial longitudinal cross-sectional view of another embodiment of a medical device, in particular, an endoscope constructed in accordance with aspects of the present invention.

FIG. 4 is a partial longitudinal cross-sectional view of another embodiment of an endoscope 320 formed in accordance with the present invention. The endoscope 320 is substantially similar in materials, construction, and operation as endoscope 20, except for the differences that will now be described. In this embodiment, the electrodes are replaced with heating devices 360, such as silicon-based heating elements, and the outer layer 330 is a thermo-responsive hydrogel that either contracts or expands in response to changes in its temperature. One non-limiting example of a hydrogel that contracts at increased temperatures is poly-isopropylacrylamide. The heating devices 360 may be connected in electrical communication with the power source 374 through the switch circuit (not shown) in such a manner as to selectively produce heat when current is supplied thereto. The switch circuit may be designed such that each heating element 360 may be individually powered to produce heat. It will be appreciated that the switch circuit may also be designed such that combinations of heating elements may be energized simultaneously, if desired.

In use, electrical current is routed to or through one or more of the heating devices 360 and, as a result, causes the heating device 360 to generate heat. The heat generated from the heating device 360 changes (i.e., increases) the ambient temperature of the hydrogel outer layer 330 in the region of the heating device 360 through heat transfer. In response to the increase in temperature, the hydrogel outer layer 330 can either expand or contract, depending on the hydrogel used, thereby releasing the drug agent 350 from the hydrogel outer layer 330.

Figure 5:
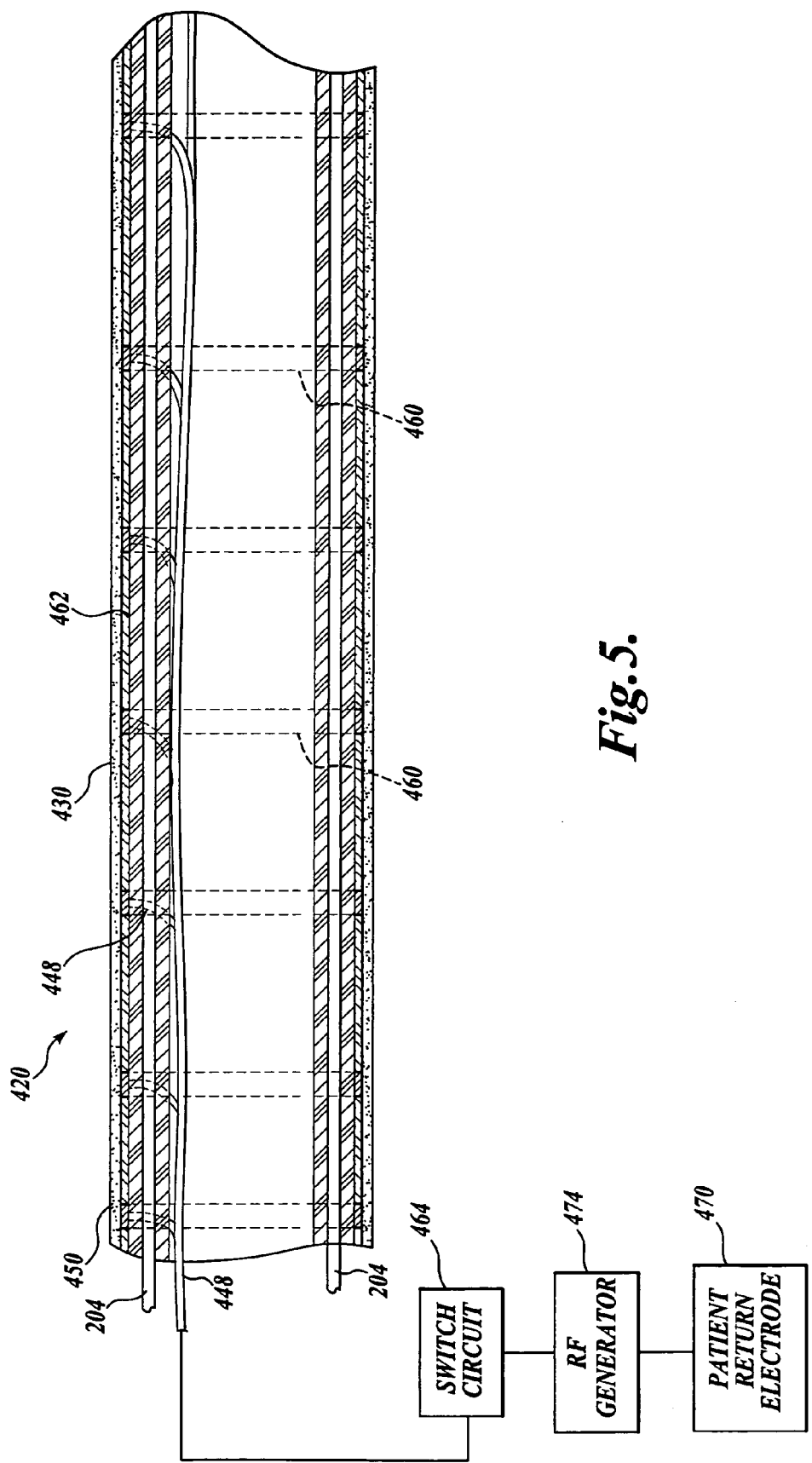
FIG. 5 is a partial longitudinal cross-sectional view of another embodiment of an endoscope formed in accordance with aspects of the present invention.

FIG. 5 illustrates another alternative embodiment of an endoscope 420 that utilizes heat as the signal or stimulus to release the drug agent 450 from its outer layer 430. The endoscope 420 is substantially similar in materials, constructions, and operation as endoscope 20, except for the differences that will now be described. In this embodiment, the electrodes 460, 470 are connected to an RF generator 474 that generates RF energy. The RF generator 474 may selectively deliver RF energy to the electrodes 460, 470 through operation of the switch circuit 464. While the embodiment of FIG. 5 illustrates a return electrode 470 that can be connected to an exterior portion of the patient in a monopolar design, the electrodes may be configured in a bi-polar design, where one reference electrode is disposed proximate to each electrode.

In use, RF energy supplied to the electrodes 460 is transmitted through at least a portion of the outer layer 430 to the return electrode 470 and, as a result, causes the ambient temperature of the outer layer 430, such as a thermo-responsive hydrogel coating, in the region of the electrodes 460 to increase. In response to the change in temperature, the outer layer 430 can either expand or contract, depending on the type of hydrogel used, thereby releasing the drug agent 450 from the hydrogel outer layer 430.

Figure 6:
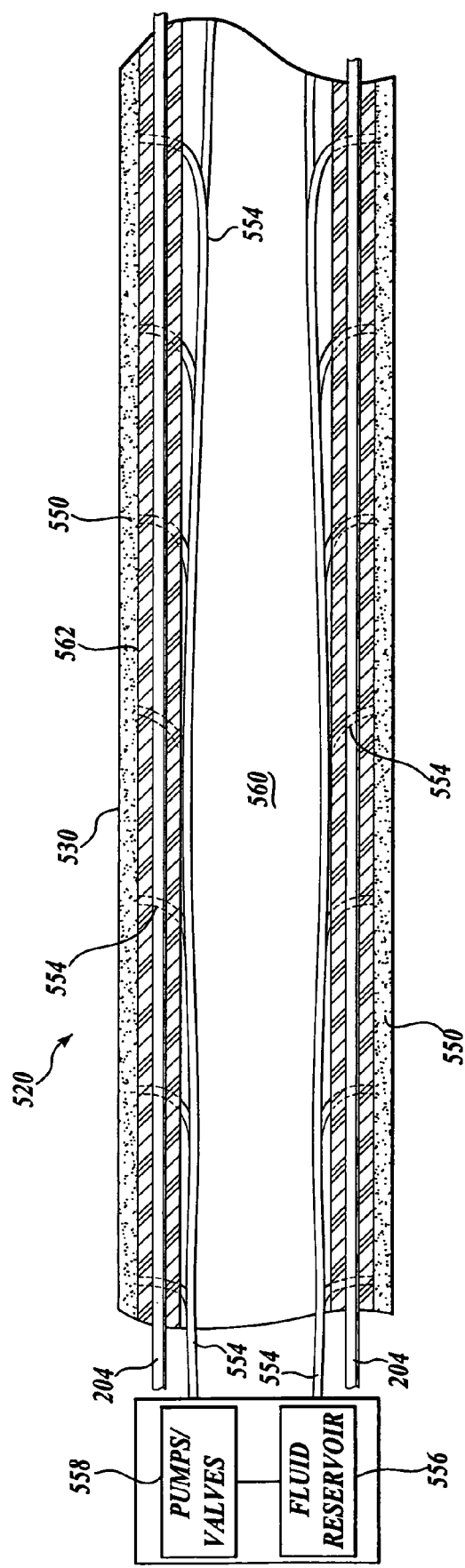
FIG. 6 is a partial longitudinal cross-sectional view of another embodiment of an endoscope formed in accordance with aspects of the present invention.

FIG. 6 illustrates another alternative embodiment of an endoscope 520 that utilizes a thermal signal or stimulus to release the drug agent from a thermo-responsive outer layer. The endoscope 520 is substantially similar in materials, construction, and operation as endoscope 20, except for the differences that will now be described. In this embodiment, the drug agent 550 is dispersed within a temperature sensitive hydrogel outer layer 530. The hydrogel outer layer 530 has low viscosity at low temperatures, and becomes solidified when its internal temperature increases. The hydrogel outer layer 530 may be affixed as a coating onto the endoscope 520 via any known techniques. To load the drug agent 550 into the outer layer 530, the endoscope 520 may be lowered into a drug agent solution at a low temperature, such as 30-50 degrees F. Upon warming the outer layer to, for example, 95-100 degrees F., the hydrogel outer layer 530 solidifies, thereby trapping the drug agent 550 therein. To release the drug agent 550 in vivo, the temperature of the outer layer 530 is lowered to "fluidize" the hydrogel outer layer.

In the aforementioned embodiment, a temperature sensitive hydrogel coating may be used as the outer layer 530. This type of temperature sensitive hydrogel coating is known as a lower critical solution temperature (LCST) material. The LCST is the temperature at which the LCST material transitions from a liquid to gel form. Suitable LCST materials that may be practiced with embodiments of the present invention include polyoxyethylene-polyoxypropylene (PEO-PPO) block copolymers. Two examples are pluronic acids 127 and F108 having molecular weights of 12,600 and 14,600, respectively. Each of these examples is commercially available from BASF of Mount Olive, N.J.

In one embodiment, pluronic acid F108 at 20%-28% concentration in phosphate buffered saline (PBS) is used as the hydrogel outer layer 530. In another embodiment, pluronic acid F108 at 22.5 concentration in phosphate buffered saline (PBS) is used as the hydrogel outer layer 530. A preparation of 22% pluronic acid F108 has an LCST of approximately 37 degrees Celsius. In yet another embodiment, pluronic acid F127 at 20%-35% concentration in phosphate buffered saline (PBS) is used at the hydrogel outer layer 530. A preparation of 20% pluronic acid 127 in PBS has an LCST of approximately 37 degrees Celsius. In these embodiments, low concentrations of dye, such as crystal violet, hormones, therapeutic agents, fillers, and antibiotics, can be dispersed in the outer layer 530. For example, a drug agent may be pre-mixed with pluronic acid F127 and the mixture is then loaded onto the shaft of the endoscope. While several examples of LCST outer layers have been described, it will be appreciated that other LCST materials that are biocompatible, biodegradable, and exist as a gel at body temperature and a liquid at below body temperature can be practiced with the present invention. The molecular weight of suitable block copolymers can be, for example, between 5,000 and 25,000.

In this embodiment, fluid delivery conduits 554 that discharge fluids such as water at temperatures lower than the outer layer's LCST in the regions of the drug agent 550 are disposed along the outer surface 562 of the endoscope. The proximal ends of the fluid delivery conduits 554 are fluidly connected to a fluid reservoir 556 via a conventional pump/valve assembly 558. It will be appreciated that the fluid delivery conduits/fluid reservoir may be integrated into the fluid wash system of the endoscope, if desired.

In use, fluid at an appropriate temperature is selectively delivered through fluid delivery conduits 554 to the outer layer 530 and, as a result, causes the ambient temperature of the outer layer 530, such as a LCST coating, in selected regions to decrease. When the temperature of the outer layer 530 decreases below its LCST by the fluid delivered thereto, the outer layer 530 transitions to a more liquid state, thereby releasing the drug agent 550 from the outer layer 530. In several embodiments, the LCST of the outer layer is approximately the internal body temperature of the patient.

Figure 7:
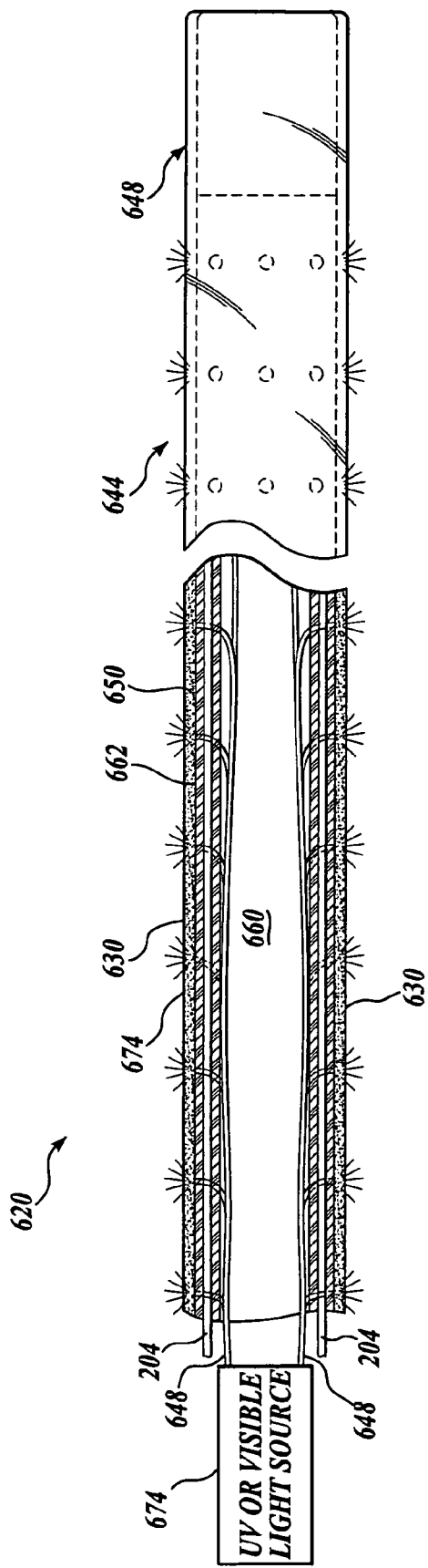
FIG. 7 is a partial longitudinal cross-sectional view of another embodiment of an endoscope formed in accordance with aspects of the present invention.

FIG. 7 is a longitudinal cross-sectional view of another embodiment of an endoscope 620 formed in accordance with the present invention, which utilizes light energy as the signal or stimulus to selectively release the drug agent 650 from a photosensitive outer layer 630. The endoscope 620 is substantially similar in materials, construction, and operation as endoscope 20, except for the differences that will now be described.

Dimensional changes such as contraction or expansion, including a transition from a liquid to a gel form and vice versa, in response to a light energy signal or stimulus may be induced in photosensitive hydrogels. Such hydrogels may contain a photosensitive compound, e.g., a chromophore, which can absorb light of a specific wavelength and induce a charge transfer that may destabilize a drug/hydrogel interaction and, thus, cause a release of the drug agent from the hydrogel. Absorption of light by the chromophore may also be dissipated as heat, thus increasing the temperature of the hydrogel that, in turn, may induce a dimensional change. For example, poly-propylacrylamide or pluronic acid can be formulated to incorporate a chromophore or chlorophyllin (trisodium salt of copper chlorophyllin). This photosensitive polymer expands (i.e., forms a gel) in the absence of light and collapses or contracts (i.e., transitions to a more liquid state) when exposed to light of a visible wavelength.

Drug agents associated with this type of photosensitive hydrogel composite can be forced out of the hydrogel as contraction of the hydrogel is induced by exposure to a visible wavelength of light. Instead of chlorophyllin, other chromophores or light-sensitive dyes, e.g., rhodamine, may be incorporated into hydrogels to alter the behavior of the hydrogel upon exposure to light.

UV light can also be used to induce a dimensional change in a drug agent-loaded hydrogel to signal drug release. Thus, in another embodiment, the light source may emit UV light into a suitable hydrogel outer layer. Suitable UV light reacting hydrogels, such as those incorporating UV-sensitive compounds, such as leucocyanide or leucohydroxide or derivatives thereof, can be used. For example, a photosensitive copolymer of N-isopropylacrylamide and bis(4-(dimethylamino)phenyl)(4-vinylphenyl) methyl leucocyanide expands when exposed to UV light and contracts when the UV light is removed. Accordingly, the release of drug agents associated with this type of outer layer can be accomplished by selectively emitting UV light from the light source, such as by turning the light generator on and off. Alternatively, drug agent release can be controlled by exposing the hydrogel to two or more different wavelengths of light, one being of a wavelength that signals the release of the drug agent and one of a wavelength that does not signal a release of the drug agent. In this embodiment, the endoscope 620 can be equipped with a light source that can be selectively controlled, i.e., by switching on or off or by altering the wavelength, to signal the release of a drug agent from a photosensitive hydrogel outer layer.

As shown in FIG. 7, a plurality of electromagnetic, radiation-emitting light sources such as fiber optic cables 648 are conventionally connected to a source of electromagnetic radiation 674. The distal ends of the fiber optic cables 648 are disposed along the endoscope outer surface 662. The distal ends of the fiber optic cabling 648 are positioned such that emission of electromagnetic radiation, e.g., visible or ultraviolet light, therefrom contacts, e.g., illuminates, a suitable photosensitive hydrogel outer layer 630 described above. The hydrogel outer layer 630 responds to the electromagnetic radiation by either contracting or expanding. The drug agent 650 is then released from the contracted or expanded outer layer 630.

FIG. 8A is a partial longitudinal cross-sectional view of another embodiment of an endoscope 720 formed in accordance with the present invention that utilizes a chemical signal or stimulus to selectively release the drug agent from a cooperating outer layer 730. The endoscope 720 is substantially similar in materials, construction, and operation as endoscope 20 and 520, except for the differences that will now be described. In this embodiment, the fluid delivery conduits 754 discharge solutions comprising chemical signals in the region of the drug agent 750 along the outer surface 762 of the endoscope. The proximal end of the fluid delivery conduits 754 are fluidly connected to a fluid reservoir 756 via a conventional pump/valve assembly 758.

In one embodiment, the outer layer 730 is an acidic or basic hydrogel coating and the discharge solution includes a pH signal or stimulus that changes the pH in the hydrogel coating, thereby causing expansion and the release of the associated drug agent 750 therefrom.

In other embodiments, the outer layer 730 may be constructed of a protein that degrades in the presence of suitable enzymes. These enzymes may be introduced to the outer layer 730 via user commands or they may be present in specified passageways through which the endoscope travels, such as the gastro tract (pepsin) or the intestinal tract (pancreatin). In the latter embodiments, the drug agent 750 carried by the protein outer layer 730 is released by exposure to the passageway, such as the GI tract. While this embodiment has been described with the outer layer 730 constructed of protein, the outer layer may be omitted and the drug agent 750 may be encapsulated with a substantially identical protein and attached to the endoscope outer surface 762 for subsequent release.

It will be appreciated that other chemical stimuli may be used with cooperatively configured outer layers to selectively release the drug agent therefrom. For example, a change in the ionic strength of a hydrogel outer layer may cause expansion or contraction, thereby releasing the drug agent therefrom.

While the fluid conduits 754 are shown in FIG. 8A as delivering the fluid or chemical stimulus to the inner surface of the outer layer 730, it will be appreciated that the fluid delivery conduits 754 may extend through the outer layer 730 and deliver the fluid or chemical stimulus to the outer surface of the outer layer 730, as best shown in FIG. 8B.

While the preferred embodiments of the invention have been illustrated and described, it will be appreciated that various changes can be made therein without departing from the spirit and scope of the invention. For example, while flexible endoscopes have been illustrated and described, rigid and semi-rigid endoscopes may also be practiced with the present invention. Additionally, one or more types of drug agents may be carried by the outer layer and selectively released therefrom. For example, the proximal region of the endoscope may carry analgesic drug agents to relieve patient discomfort while the distal end may include therapeutic drug agents. It is therefore intended that the scope of the invention be determined from the following claims and equivalents thereof.

The embodiments of the invention in which an exclusive property or privilege is claimed are defined as follows:

1. A method of selectively releasing an analgesic drug agent from an endoscope in vivo, said method comprising:
routing an endoscope through an intestinal tract of a patient's body, wherein said endoscope comprises: (a) a shaft having proximal and distal ends, a working channel lumen, and an outer surface; (b) a hydrogel outermost layer disposed on a portion of the outer surface of the shaft; (c) an analgesic drug agent carried in or on a portion of the hydrogel outermost layer; (d) three or more electrodes spaced apart along a length of the endoscope in contact with the outermost layer, wherein each of the electrodes is adapted to be individually selectively energized; and (e) a stimulus generator associated with the endoscope, the stimulus generator, based upon a selective input, generating an electrical stimulus that causes the drug agent to be released from the hydrogel outermost layer; and
selectively energizing said electrodes to release the analgesic drug agent from the hydrogel outermost layer, wherein the analgesic drug agent is delivered locally to a wall of the intestinal tract for relieving patient discomfort.

2. The method of claim 1, wherein selectively releasing of the drug agent includes user input.

3. The method of claim 1, wherein selectively releasing the drug agent includes input based upon environmental conditions.

* * * * *